March 6, 1973 D. L. ARMSTRONG Plant Pat. 3,315
ROSE PLANT
Filed April 15, 1971
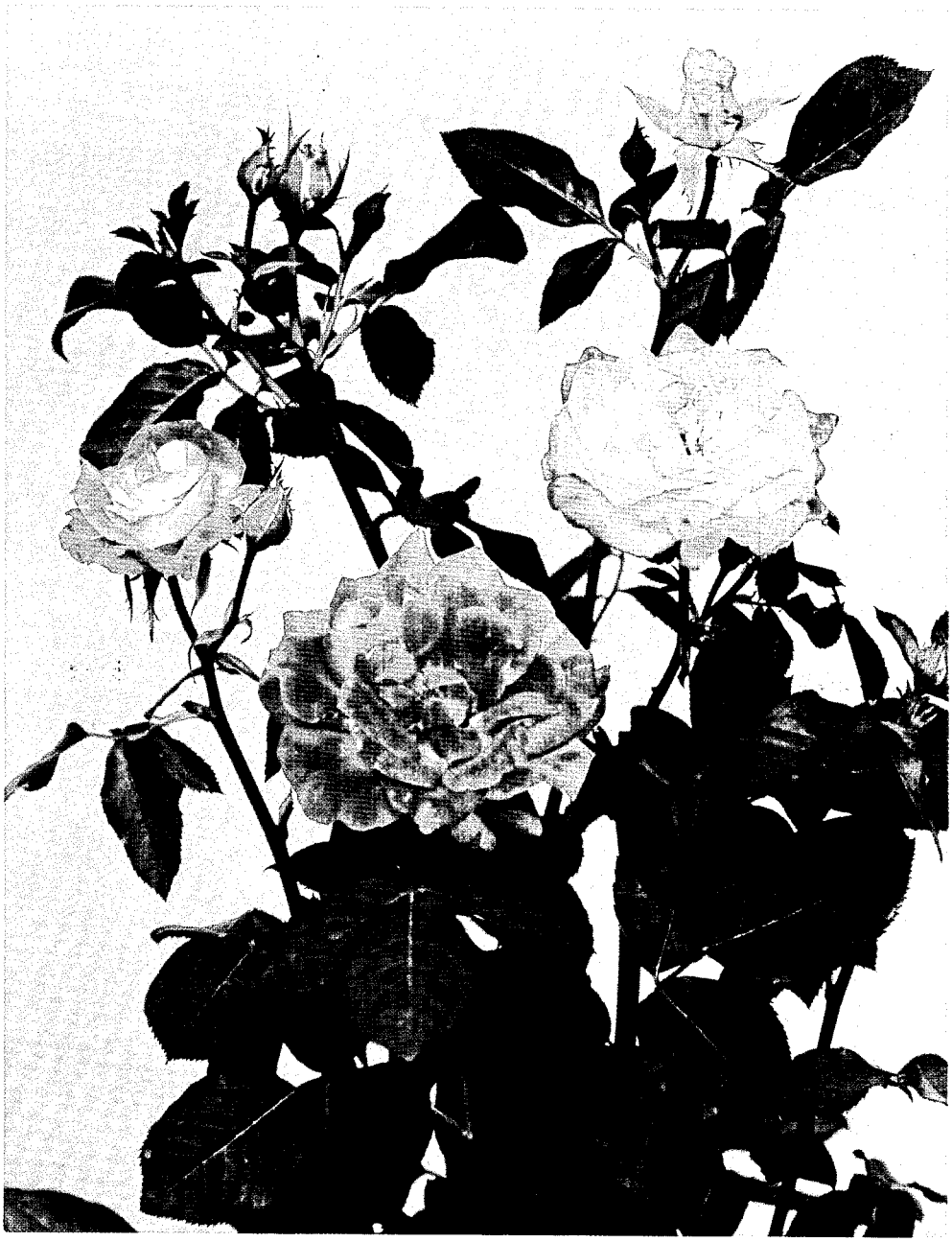

United States Patent Office

Plant Pat. 3,315
Patented Mar. 6, 1973

3,315
ROSE PLANT

David L. Armstrong, Upland, Calif., assignor to Armstrong Nurseries, Inc., Ontario, Calif.

Filed Apr. 15, 1971, Ser. No. 134,518
Int. Cl. A01h 5/00
U.S. Cl. Plt.—22 1 Claim

ABSTRACT OF THE DISCLOSURE

A rose plant of the floribunda class which bears blooms that are large for this class, on normal medium-length stems. Most blooms occur in irregular clusters of three to four, or more, flowers, although some blooms may be borne singly. The flower may span as much as four inches when fully open, and usually contains from 20 to 25 quite broad petals. The plant blooms freely outdoors, and nearly continuously during the growing season. The general color effect of the newly opened flower is yellow-pink and red, the yellow being notable. The fragrance is a blend of damask rose and spice, and is moderately penetrating to strong.

This invention relates to a new rose plant of the floribunda class. The plant is a seedling of the moderately tall, bushy, outdoor type, cultivated for cut flowers primarily and for garden decoration. It was propagated by David L. Armstrong in Ontario, Calif., having as its seed parent "Circus" and, as its pollen parent, "Texan." It holds its distinguishing characteristics through succeeding propagations by budding.

The new variety sometimes bears its flowers singly, on normal, medium-length stems. Usually, however, the flowers are borne in irregular clusters of from three to four, or more blooms. The plant blooms freely outdoors, and nearly continuously during the growing season. It has a moderately penetrating to strong fragrance, suggesting a blend of damask rose and spice.

This new variety of rose plant differs from its seed parent, Circus, Plant Patent No. 1,382, in the following particulars:

As to the bloom, the flowers of this plant are substantially larger, being from 3½" to 4" in diameter, whereas the flowers of Circus are usually from 2½" to 3". Furthermore, the petals of this variety are broader, and only about half as numerous. While this flower may have from 20 to 25 petals, plus a few to half a dozen petaloids, Circus normally has from 45 to 58 petals. The color of the bloom displays substantially more red pigment, at all stages of the flower, than is observed in the bloom of Circus.

In the new variety, the prickles on the peduncles are substantially more numerous and also somewhat larger than is typical of Circus.

Although the flowers of this new cultivar are larger, the clusters do not usually contain as many flowers, nor does the plant bear as many flowers, over all, even though it is somewhat larger than Circus.

The fragrance of the new cultivar, although similar to that of Circus, is substantially more intense and penetrating. The fragrance of Circus flowers suggests a blend of tea and spice, but this new cultivar more nearly resembles the fragrance of damask roses blended with spice.

The new variety is distinct from its pollen parent, Texan, Plant Patent No. 1,471, in the following particulars:

Whereas the overall color effect of the flowers of this new variety display a blend of yellow-pink and red, the flowers of Texan are described as rose red. The yellow quality of dominates in the new plant and the red in Texan.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is short to average length, and of average caliper, erect, and with numerous stipitate glands and small prickles. Its color is near Strong Yellow Green, 2.5GY 6/8, overlaid with near Dark Greenish Yellow, 7.5Y 6/7 on the side exposed to the sun.

Before the calyx breaks, the bud is small, short and ovid in form.

As the calyx breaks, the color is near Dark Reddish Orange, 7.5R 4/11. The inner surface of the sepals carries a fine, wooly tomentum.

The margins of alternate sepals are lined with a fine, woolly tomentum; margins of others are lined with many small stipitate glands and small slender foliaceous parts. Most of these foliaceous parts also have several small stipitate glands along the edges. The outside surface of the sepals carries many stipitate glands. Sometimes the sepals have foliaceous appendages equal to about one-quarter of the sepal length.

As the first petal opens, the bud is small, but large for this class of rose, short to medium-length, pointed to ovoid in form, and usually urn-shaped. The color on the outside of the petal is between Strong Reddish Orange, 7.5R 5/13, and Vivid Red, 5R 5/13. The inside surface of the petal is near Strong Reddish Orange, 10R 6/12, blending with near Strong Orange, 2.5YR 7/10, toward the base of the petal. The bud opens up well, and is not retarded or prevented from opening by cold, hot, wet, or dry weather.

Bloom

The size of the bloom when fully open is from average to large for the floribunda class, being from 3½ inches to 4 inches across. The petalage is double, with from 20 to 25 petals, plus 3 to 6 petaloids arranged irregularly. The bloom is high centered at first, becoming flat to high centered.

At first the petals are tightly cupped, with tips rolled outward, becoming later at maturity loosely cupped, with tips rolled outward. The inner petals on the newly opened flower have tips rolled outward; the intermediate and outer petals of the newly opened flower are rolled outward, both along the apex and the edges. All petals on a three days open flower rolled outward both along the apex and the edges.

The petals are of medium thickness, with inside velvety and outside satiny. The outside petals are between round and broadly obovate, with apex flat, and usually with 1 to 2 notches. Both the intermediate and inside petals are obovate, with apex rounded, sometimes with 1 or 2 notches. The colors may be modified by being shaded and/or washed with other colors.

The paragraphs immediately following describe color values observed in a flower newly opened in the month of September. The plant had been grown outdoors, in Ontario, Calif.

The outer surface of the outside petal is between Deep Purplish Pink, 7.5RP 6/12, and Strong Pink, 10RP 7/8, a small area at the base of the petal being near Brilliant Greenish Yellow, 7.5Y 9/8. The inner surface of the outside petal is near Strong Red, 5R 4/12, blending with near Strong Yellowish Pink, 5R 7/9, toward the base of the petal, and also with a small area at the base of petal near Vivid Greenish Yellow, 7.5Y 8/12.

The outer surface of the intermediate petal is near Deep Pink, 2.5R 6/11, blending with near Light Orange, 2.5YR 8/6, toward the base of the petal, with a small area at the base of the petal being near Brilliant Yellow, 2.5Y 9/9. The inner surface of the intermediate petal is near Moderate Yellowish Pink, 7.5R 8/6, with a small area at the base of the petal being near Vivid Yellow, 5Y 8/12.

Both the outer surface and the inner surface of the inner petal have the same color characteristics as the intermediate petal.

The paragraphs immediately following describe the color values observed in a bloom which had been open for three days, outdoors, in the month of September. The plant had been grown outdoors, in Ontario, Calif.

The outer surface of the outside petal was near Strong Purplish Red, 10RP 4/12, blending with near Light Purplish Pink, 7.5RP 8/5, toward the base of the petal. The inner surface of the outside petal was near Strong Red. 5R 4/12, blending with near Light Purplish Pink, 7.5RP 8/5, toward the base of the petal.

The outer surface of the inside petal was near Moderate Pink, 10RP 8/5, blending with near Light Purplish Pink, 7.5RP 8/5, toward the base of the petal. The inner surface of the inside petal was near Strong Red, 5R 4/12, blending with near Strong Yellowish Pink, 5R 7/9, toward the base of the petal.

The general color effect of the newly opened flower is from Strong Red, 5R 4/12, to Strong Yellowish Pink, 7.5R 7/9. The bloom after being three days open gives a general color effect of between Strong Red, 5R 4/12, and Strong Red, 2.5R 5/12. The petals drop off cleanly, and are not particularly affected by cold, hot, wet, or dry weather.

The flower on the bush in the garden persists for from 3 to 4 days in the month of August, in the locality named. Cut roses grown outdoors and kept at living-room temperatures will last from 3 to 4 days in the month of August.

*Reproductive organs*

Stamens: The stamens are average in number, arranged regularly about the pistils, a few mixed with petaloids.

Filaments: The filaments are short to medium length, being 5 to 8 mm. in length, and near Vivid Yellow, 2.5Y 8/12, in color. Most are with anthers.

Anthers: The anthers are small in size, all opening approximately at once. On both the upper and lower sides the margins are near Strong Orange Yellow, 10YR 7/10, and the remaining area is near Brilliant Yellow, 5Y 9/9.

Pollen: The pollen is moderate in quantity and of a color which is near Strong Orange Yellow, 7.5YR.

Pistils: The pistils are approximately 50 in number, this being average.

Styles: The styles are uneven, short, thin caliper, and bunched. The upper one-third of the style is near Strong Red, 5R 4/12; the remainder near Brilliant Greenish Yellow, 10Y 9/9.

Stigma: The stigma is near Strong Orange Yellow, 10YR 7/10.

Ovaries: The ovaries are usually all enclosed in the calyx.

Hips: The hips are average in length, but this may vary. They are vase shaped to oblate, with inconspicuous neck. They are smooth to slightly tomentose, with thick, fleshy walls. Their color is not significant.

Sepals: The sepals are permanent. They are of short to medium length, straight, and spear-shaped to recurved. The color is not significant, either inside or outside.

Seeds: This new variety produces no seeds naturally.

*Foliage*

The compound leaves usually comprise three to seven leaflets. They are abundant, medium size, leathery, and semi-glossy in texture. The leaflets are ovate, but with apex acute to acuminate, base round to cuneate, and margin simply serrate.

The mature foliage displays upon its upper surface a near Grayish Olive Green, 5GY 3/2. The under surface is near Moderate Yellow Green, 7.5GY 5/7.

The young foilage on its upper surface is near Moderate Olive Green, 7.5GY 4/4; on its under surface it is near Moderate Yellow Green, 5GY 5/6.

The rachis is average in size, its upper side being grooved, with some small stipitate glands on the edges. The underside has many small prickles and numerous stipitate glands.

The stipules are medium-length to long, narrow, with short points turning out at an angle of more than 45°.

The plant displays a more than average resistance to mildew, when compared with other varieties now in commerce and grown under comparable conditions at Ontario, Calif.

*Growth*

The plant is of upright-spreading free-growing habit, and much branched. Its canes are of medium caliper.

The main stems are near Moderate Yellow Green, 5GY 5/6, in color. They bear several large prickles which are medium-length, hooked slightly downward, with long narrow base. Their color is near Strong Brown, 5YR 4/5. There are a few small prickles, and their color is the same as that of the large prickles. There are no hairs.

The branches are a color near Moderate Yellow Green, 5GY 5/6. They carry several to many large prickles which are medium-length, hooked slightly downward, with long narrow base. Their color is near Brownish Orange, 5YR 5/8. There are a few small prickles, and their color is the same as that of the large prickles. There are no hairs.

New shoots are near Strong Yellow Green, 5GY 6/8, in color. There are a few large prickles of short to medium-length, hooked slightly downward, with long narrow base. Their color is near Light Olive, 5Y 5/6. There are a few small prickles, and their color is the same as that of the large prickles. There are no hairs.

I claim:

1. The new variety of rose plant of the floribunda class, substantially as herein shown and described, manifesting in combination a plurality of the following features, namely, a free and upright-spreading habit of growth, with foliage and peduncles having a better than average resistance to mildew, the foliage comprising an abundant quantity of dark green leaves, and the peduncles bearing numerous stipitate glands and small prickles; the flowers of the plant being comparatively large for the floribunda class, and ranging upwards to about four inches in diameter; each flower comprising petals which, though comparatively few in number, are unusually wide, and impart a progression of color from bud to finished bloom which is distinguished by the pronounced development of yellow color values against red in the freshly opened bloom to strong red color values at maturity; the fragrance of said flowers being a moderate to strong and penetrating odor suggesting a combination of spice and damask rose.

No references cited.

ROBERT E. BAGWILL, Primary Examiner